United States Patent
Furuya et al.

(12) 
(10) Patent No.: US 6,274,553 B1
(45) Date of Patent: Aug. 14, 2001

(54) METHOD FOR STABILIZING PEPTIDES AND FREEZE-DRIED MEDICINAL COMPOSITIONS CONTAINING PEPTIDES OBTAINED BY USING THE METHOD

(75) Inventors: Hideyuki Furuya, Saitama; Hiroyuki Morita; Yukitaka Takatsu, both of Tokyo; Kose Michibuchi; Makoto Tanigawa, both of Shiga, all of (JP)

(73) Assignee: Japan Energy Corporation, Tokyo (JP)

( * ) Notice: Subject to any disclaimer, the term of this patent is extended or adjusted under 35 U.S.C. 154(b) by 0 days.

(21) Appl. No.: 09/341,926

(22) PCT Filed: Jan. 19, 1998

(86) PCT No.: PCT/JP98/00178

§ 371 Date: Dec. 21, 1999

§ 102(e) Date: Dec. 21, 1999

(87) PCT Pub. No.: WO98/31386

PCT Pub. Date: Jul. 23, 1998

(30) Foreign Application Priority Data

Jan. 20, 1997 (JP) .................................................. 9-020957

(51) Int. Cl.$^7$ .............................. A61K 38/00; C07K 7/10
(52) U.S. Cl. .................................. 514/12; 514/19; 514/21; 514/784; 514/822; 514/970; 530/324; 530/855
(58) Field of Search .................................. 514/12, 21, 19, 514/784, 822, 970; 530/324, 855

(56) References Cited

U.S. PATENT DOCUMENTS

| | | | |
|---|---|---|---|
| 4,409,334 | 10/1983 | Lill et al. ................................. | 436/8 |
| 4,654,302 | * 3/1987 | Fritz et al. ............................... | 435/70 |
| 5,059,587 | * 10/1991 | Yamamoto .............................. | 514/12 |
| 5,164,304 | 11/1992 | Johnson et al. ....................... | 435/69.1 |
| 5,286,714 | * 2/1994 | Crause et al. .......................... | 514/12 |
| 5,356,875 | 10/1994 | Sarmientos et al. .................... | 514/12 |
| 5,472,938 | * 12/1995 | Arvinte ..................................... | 514/6 |
| 5,484,890 | 1/1996 | Johnson et al. ....................... | 530/383 |
| 5,541,161 | 7/1996 | Krstenansky et al. ................. | 514/14 |
| 5,607,714 | 3/1997 | Connolly .............................. | 426/599 |
| 5,616,476 | 4/1997 | Crause et al. ....................... | 435/69.1 |
| 5,747,447 | 5/1998 | Swift et al. ............................... | 514/9 |

FOREIGN PATENT DOCUMENTS

| | | |
|---|---|---|
| 38045/89 | 1/1990 | (AU) . |
| 60-136597 | 7/1985 | (JP) . |
| 2117694 | 5/1990 | (JP) . |
| 4327539 | 11/1992 | (JP) . |
| 5247090 | 9/1993 | (JP) . |
| 7267877 | 10/1995 | (JP) . |
| 9227407 | 9/1997 | (JP) . |
| WO 96/27661 | * 9/1996 | (WO) . |

* cited by examiner

*Primary Examiner*—Christopher S. F. Low
*Assistant Examiner*—Abdel A. Mohamed
(74) *Attorney, Agent, or Firm*—Testa, Hurwitz & Thibeault

(57) ABSTRACT

A method is provided for elevating the stability of peptides containing the sequence -Asp-Gly- or -Asn-Gly- by preventing these sequences from changing into succinimide compounds or β-transition compounds. The method comprises adding an organic acid to a solution of peptides containing these sequences to bring the pH value of the solution to a pH of between 5 and 6.5 followed by freeze-drying. In one embodiment, sucrose or mannitol is added together with the organic acid. Freeze-dried medicinal compositions obtained by using the method have excellent stability. In one embodiment of the invention, compositions produced by the method are provided and comprise hirudin or hirudin variants.

27 Claims, 1 Drawing Sheet

METHOD FOR STABILIZING PEPTIDES AND FREEZE-DRIED MEDICINAL COMPOSITIONS CONTAINING PEPTIDES OBTAINED BY USING THE METHOD

TECHNOLOGICAL FIELD OF THE INVENTION

The present invention relates to a method for stabilizing and controlling change in a peptide which comprises a sequence -Asp-Gly- or -Asn-Gly- in the amino acid sequence, wherein the sequence -Asp-Gly- or -Asn-Gly- changes into a succinimide moiety by a dehydration reaction or a deamidation reaction and further changes into a β-rearranged moiety by an isomerization reaction, particularly to a method for controlling such a change in a peptide such as desulfatohirudin or a hirudin variant. The present invention also relates to a lyophilized pharmaceutical composition containing a peptide for which the change is controlled by this stabilizing method.

BACKGROUND OF THE INVENTION

Hirudin is an anti-blood coagulation factor which is secreted from the salivary glands of Hirudo medicinal is. Since hirudin exhibits an anti-thrombin activity, this compound and its variants are used as anti-blood coagulation drugs.

The hirudin and most hirudin variants contain a sequence of -Asp-Gly- or -Asn-Gly- and change into succinimide compounds due to a change in this sequence with the passage of time. The succinimide compounds further change into β-rearranged compounds. Because of this, even if the compounds are sufficiently purified in the production line, the purity of the compounds decreases with the passage of time due to production of the succinimide compounds and β-rearranged compounds. Because the succinimide compounds and β-rearranged compounds exhibit anti-thrombin activity themselves (Japanese Patent Application Laid-open No. 310788/1993), such a decrease in purity does not cause serious problems in general. However, such deterioration of the purity is not desirable when these compounds are used as drugs. Therefore, various studies have been undertaken to improve the stability of hirudin.

Examples of them include a method of adding a water-soluble salt of calcium and/or magnesium to hirudin to increase the stability of hirudin (Japanese Patent Application Laid-open No. 267877/1995), a method of adding potassium phosphate and sugar (WO 95/20399), and the like. However, these proposed methods cannot accomplish sufficiently increase in the stability of hirudin.

DISCLOSURE OF THE INVENTION

The present invention has been achieved to overcome these problems.

Specifically, an object of the present invention is to provide a method for stabilizing a peptide containing a sequence -Asp-Gly- or -Asn-Gly-, which comprises controlling change of the sequence -Asp-Gly- or -Asn-Gly- into a succinimide moiety or a β-rearranged moiety.

Another object of the present invention is to provide a hirudin-containing lyophilized pharmaceutical composition with excellent stability by utilizing this stabilizing method.

The above object is achieved in the present invention by a stabilization method comprising:

providing a solution of a peptide which contains a sequence -Asp-Gly- or -Asn-Gly- which may be converted into a succinimide moiety shown by the following general formula (1),

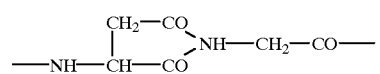

or a β-rearranged moiety shown by general formula (2),

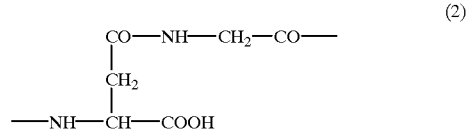

adding an organic acid and adjusting the pH of the solution to 5–6.5, and lyophilizing the resulting mixture.

Desulfatohirudin or a hirudin variant is used as the peptide in the present invention.

The above object is further achieved in the present invention by a pharmaceutical composition prepared using the above-mentioned stabilization method of peptide, specifically by a hirudin-containing lyophilized pharmaceutical composition comprising 5 to 100 mol of an organic acid added to one mol of desulfatohirudin or a hirudin variant. In a preferred embodiment of the present invention, in addition to the organic acid, 1 to 500 mol of saccharose and, as required, 10 to 1000 mol of mannitol, for one mol of desulfatohirudin or a hirudin variant, are added to the peptide solution to be lyophilized.

BEST MODE FOR CARRYING OUT THE INVENTION

Figure 1:
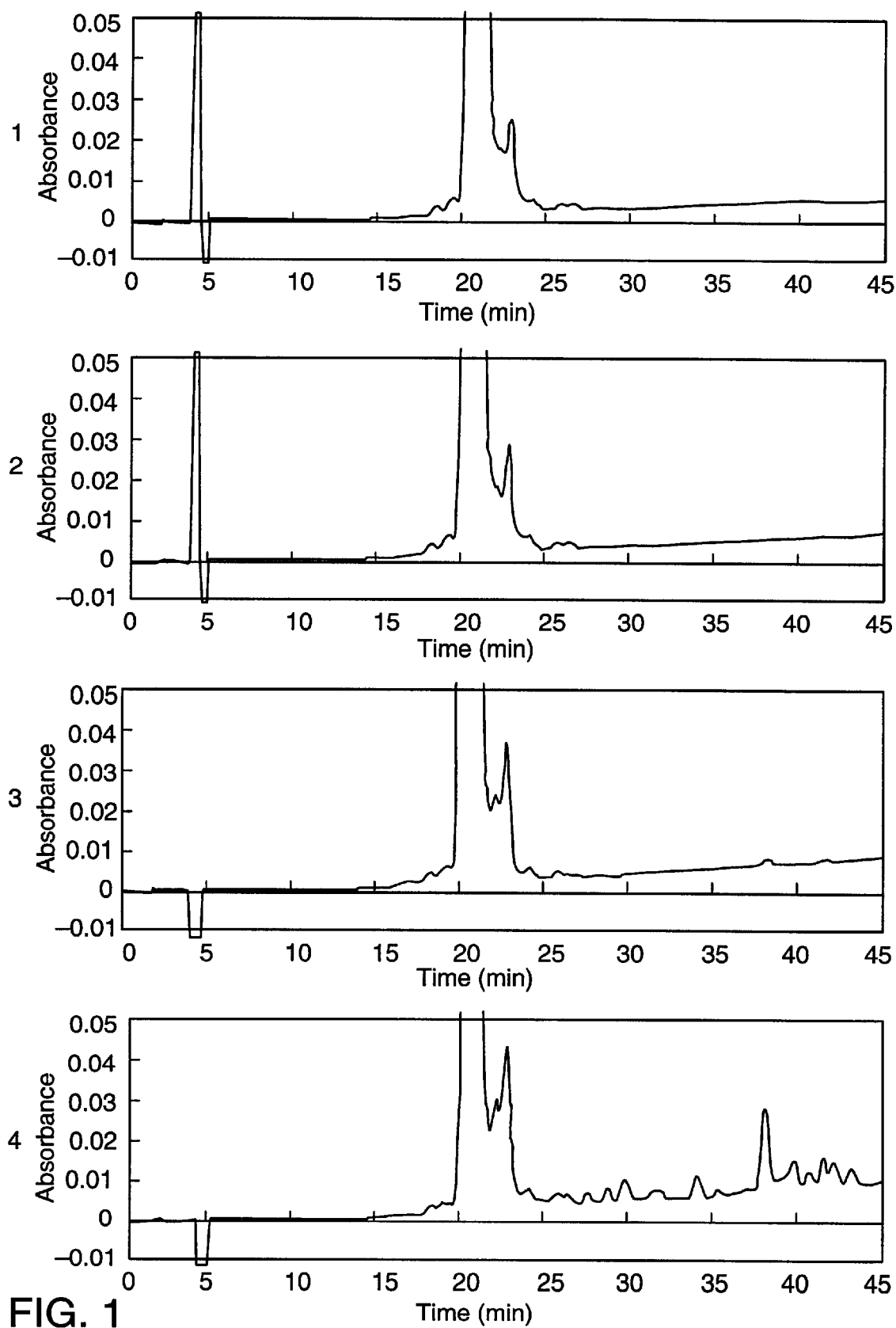
FIG. 1 shows chromatograms produced by liquid chromatography when lyophilized samples which had been preserved in an incubator at 40° C. for 3 months were analyzed in the Experiment Example 6, wherein the numbers indicate prescription numbers therein.

The method of the present invention can be applied to a peptide including the amino acid sequence -Asp-Gly- or -Asn-Gly- to control the change of these moieties into a succinimide moiety of the general formula (1) or β-rearranged moiety of the general formula (2) with the passage of time. The present invention therefore can be applied to all peptides containing the sequence -Asp-Gly- or -Asn-Gly-, such as desulfatohirudin HV-1 (Japanese Patent Application Laid-open No. 136597/1985), HV-2 (Harvey et. al., Proc. Natl. Acad. Sci. 83, 1084 (1986)), a hirudin variant HV1C3 shown by Sequence No. 1 (Japanese Patent Application Laid-open No. 173798/1992), a human growth hormone, or lysozyme, with a particularly preferred peptide being the hirudin variant HV1C3 (Sequence Table, Sequence No. 1). Further included in the peptides to which the method of the present invention is applicable are various hirudin variants derived from the desulfatohirudin HV-1 or hirudin variant HV1C3 by modification of the amino acid sequence, while preserving the sequence -Asp-Gly- or -Asn-Gly-. Specific examples are rHV-1-9 (Sequence Table, SEQ. ID NO:2), rHV-1-10 (Sequence Table, SEQ. ID NO:3), rHV-1-14 (Sequence Table, SEQ. ID NO:4), rHV-1-15 (Sequence Table, SEQ. ID NO:5), and rHV-1-16 (Sequence Table, SEQ. ID NO:5) described in European Patent Publication EP 0625580 A1, or HV-17 (Sequence Table, SEQ. ID NO:7) described in WO 92/15610.

In the present invention, such a peptide is first dissolved in water to a final concentration of 0.1 to 500 mM. Then, the solution is adjusted to a pH of between 5 and 6.5 with the addition of an organic acid and, as required, an aqueous alkaline solution such as an aqueous solution of sodium hydroxide. Various pharmaceutically acceptable carboxylic acids can be used as the organic acid. Examples of such carboxylic acids include monobasic acids such as acetic acid and lactic acid, and dibasic or tribasic acids such as tartaric acid, citric acid, and malic acid. Of these, particularly preferred in view of their superior effect in stabilizing peptides are tartaric acid and citric acid from the dibasic and tribasic acids and acetic acid from the monobasic acids. More generally, a carboxylic acid having a structure in which a hydroxyl group is substituted on the α position carbon, specifically, a chain carboxylic acid containing a structure of C—CH(OH)—COOH, particularly those from a dibasic acid or a tribasic acid, is preferred. If the pH of the aqueous solution of peptide is greater than 6.5 or less than 5, the product by lyophilizing such apeptide solution has very poor stability.

In the case of the above-described desulfatohirudin or hirudin variant, it is desirable to add from 5 to 100 mM of organic acid for 1 mM of the hirudin and further to add an aqueous alkaline solution, as required, to adjust the pH in the range from5 to 6.5. A hirudin-containing lyophilized pharmaceutical composition can be obtained by lyophilization of this solution. In this instance, the product obtained by lyophilization of a mixture with only an added organic acid is a soft material, somewhat like down or fluff, which is hard to handle in preparation and administration. Therefore, it is desirable to add from 1 to 500 mM of saccharose for 1 mM of hirudin as a vehicle, in addition to an organic acid. It is more desirable to further add 10 to 1000 mM of mannitol for 1 mM of hirudin. There are no limitations to the order of carrying out these operations for the pH adjustment by the addition of organic acid, the addition of saccharose, and the addition of mannitol. Any one of these components may be added first or all components may be added simultaneously.

It is desirable that the peptide solution thus prepared be isotonic. This solution is lyophilized by a conventional method. The lyophilized product can be re-dissolved and instantly used as a drug.

The features of the present invention will now be described specifically by way of experiment examples. In the examples, the contents of various components added to pharmaceutical compositions indicate the final concentration of the components in the peptide solution to be lyophilized for the preparation of these pharmaceutical compositions. Indicated pH values also indicate the pH of the peptide solution to be lyophilized.

EXAMPLES

Experiment Example 1

Hirudin variant HV1C3 having the amino acid sequence shown by Sequence NO. 1 in the Sequence Table, glycine, and mannitol were dissolved in purified water to a final concentration of 6 mg/ml (0.86 mM), 6.7 mg/ml (89 mM), and 33.5 mg/ml (184 mM), respectively. The resulting solution was divided into six equal portions. These portions were adjusted to the pH shown in Table 1 with the addition of 30 mM of tartaric acid, phosphoric acid, or Tris buffer solution. The peptide solutions for which the pH was thus adjusted filtered through a 0.22 µm membrane filter. The filtrates were charged into 6 ml vials in the amount of 1 ml for each vial. 50 such vials were prepared for each pH of the solution, totaling 300 vials. All these 300 vials were lyophilized.

The lyophilized samples were stored in an incubator at 50° C. and removed from the incubator after 1, 2, 4, 6, 8 weeks, respectively. 1 ml of purified water was added to each vial removed. Solutions further diluted 50-fold were subjected to liquid chromatography to measure a peak area percentage of hirudin variant HV1C3 under the conditions shown in Table 2. The amount (percentage) of the hirudin variant HV1C3 remaining in the lyophilized sample, after having been stored in the incubator, compound with the amount of the hirudin variant HV1C3 contained at the beginning of the storage was determined. The results are shown in Table 1.

TABLE 1

| pH adjustment | Remaining peptide (%) | | | | |
|---|---|---|---|---|---|
| pH agent | 1 wk | 2 wks | 4 wks | 6 wks | 8 wks |
| 4.5 Tartaric acid | 98.0 | 97.7 | 95.4 | 94.7 | 93.4 |
| 5.5 Tartaric acid | 98.6 | 98.7 | 97.5 | 96.5 | 97.0 |
| 6.0 Phosphoric acid | 98.4 | 96.4 | 95.1 | 94.5 | 93.6 |
| 7.0 Phosphoric acid | 99.0 | 97.3 | 93.3 | 92.7 | 90.0 |
| 7.0 Tris buffer | 95.7 | 92.0 | 86.8 | 72.0 | 70.3 |
| 8.0 Tris buffer | 81.9 | 58.0 | — | — | — |

TABLE 2

| | |
|---|---|
| Detector: | Ultraviolet spectrophotometer |
| Column: | YMC Protein-RP (inner diameter 7.5 mm, length 25 cm) |
| Column temperature: | 30° C. |
| Running buffer A: | Trifluoroacetic acid aqueous solution (0.2 vol %) |
| Running buffer B: | Trifluoroacetic acid acetonitrile solution (0.2 vol %) |
| Running buffer gradient: | Running buffer B is linearly increased by 10% from 17% to 27% in 40 minutes after sample was charged. |
| Flow rate: 1.0 ml/min | |

It can be seen from the above results that lyophilizing the samples after adjusting the pH to 5–6.5 ensures superior stability.

Experiment Example 2

Hirudin variant HV1C3, purified saccharose, and mannitol were dissolved in purified water to a final concentration of 6 mg/ml (0.86 mM), 1.6 mg/ml (4.7 mM), and 10 mg/ml (55 mM), respectively. The resulting solution was divided into five equal portions. Four of these portions were adjusted to pH 5.5 with the addition of 30 mM of acetic acid, tartaric acid, citric acid, or phosphoric acid. The peptide solutions for which the pH was thus adjusted and the peptide solution without pH adjustment were filtered through a 0.22 µm membrane filter. The filtrates were filled into 6 ml vials in the amount of 1 ml for each vial. 50 such vials were prepared for each pH of the solution, 250 vials in total. All these 250 vials were lyophilized.

The lyophilized samples were stored in an incubator at 60° C. and removed from the incubator after 1, 2, 3, 4, 5, 6, 7, and 8 weeks, respectively. 1 ml of purified water was added to each vial removed. Solutions further diluted 50-fold were used to measure the amount (percentage) of the hirudin variant HV1C3 remaining in the lyophilized sample in the same manner as in Experiment Example 1. The results are shown in Table 3.

TABLE 3

| pH Adjusting agent | Remaining peptide (%) | | | | | | | |
|---|---|---|---|---|---|---|---|---|
| | 1 wk | 2 wks | 3 wks | 4 wks | 5 wks | 6 wks | 7 wks | 8 wks |
| — | 96.9 | 94.2 | 92.3 | 90.9 | 89.9 | 88.2 | 87.2 | 86.1 |
| Acetic acid | 98.3 | 95.6 | 94.2 | 93.3 | 92.0 | 91.9 | 91.4 | 90.6 |
| Tartaric acid | 98.4 | 97.6 | 95.9 | 95.2 | 92.4 | 92.2 | 91.9 | 90.6 |
| Citric acid | 97.4 | 95.8 | 94.4 | 93.3 | 92.4 | 91.6 | 90.8 | 89.8 |
| Phosphoric acid | 77.9 | 66.6 | 61.4 | 58.1 | 57.3 | 57.6 | — | — |

It can be seen from the above results that stability is improved by lyophilizing samples after adjusting the pH by the addition of an organic acid. However, the stability cannot be improved using phosphoric acid which is an inorganic acid.

Experiment Example 3

Hirudin variant HV1C3, purified saccharose, and mannitol were dissolved in purified water to a final concentration of 6 mg/ml (0.86 mM), 1.6 mg/ml (4.7 mM), and 10 mg/ml (55 mM), respectively. The resulting solution was divided into four equal portions. Three of these portions were adjusted to pHs 5.0, 5.5, and 6.0 using 30 mM tartaric acid. The peptide solutions for which the pH was thus adjusted and the peptide solution without pH adjustment were filtered through a 0.22 μm membrane filter. The filtrates were filled into 6 ml vials in the amount of 1 ml for each vial. 50 such vials were prepared for each pH of the solution, 200 vials in total. All these 200 vials were lyophilized.

The lyophilized samples were stored in an incubator at 60° C. and removed from the incubator after 1, 2, 3, 4, 5, 6, 7, and 8 weeks, respectively. 1 ml of purified water was added to each vial removed. Solutions further diluted 50-fold were used to measure the amount (percentage) of the hirudin variant HV1C3 remaining in the lyophilized sample in the same manner as in Experiment Example 1. The results are shown in Table 4.

TABLE 4

| pH | Remaining peptide (%) | | | | | | | |
|---|---|---|---|---|---|---|---|---|
| | 1 wk | 2 wks | 3 wks | 4 wks | 5 wks | 6 wks | 7 wks | 8 wks |
| — | 96.9 | 94.2 | 92.3 | 90.9 | 89.9 | 88.2 | 87.2 | 86.1 |
| 5.0 | 97.6 | 96.1 | 93.2 | 91.8 | 91.7 | 89.9 | 69.1 | 86.6 |
| 5.5 | 98.4 | 97.6 | 95.9 | 95.2 | 92.4 | 92.2 | 91.9 | 90.6 |
| 6.0 | 98.4 | 97.6 | 96.6 | 96.1 | 94.6 | 93.6 | 91.8 | 92.2 |

It can be seen from the above results that stability is remarkably improved by adjusting the pH to 5–6.5 using an organic acid, particularly tartaric acid.

Experiment Example 4

Hirudin variant HV1C3 and purified saccharose were dissolved in purified water to a final concentration of 6 mg/ml (0.866 mM) and 1.6 mg/ml (4.7 mM), respectively. The resulting solution was divided into four equal portions. Three of these portions were adjusted to pH 5.5 using 5 mM of tartaric acid, 10 mM of tartaric acid, and 30 mM of tartaric acid, respectively. Mannitol was added to a solution without pH adjustment to a concentration of 10 mg/ml (55 mM). These solutions were filtered through a 0.22 μm membrane filter. The filtrates were filled into 6 ml vials in the amount of 1 ml for each vial. 50 such vials were prepared for each pH of the solution, 200 vials in total. All these 200 vials were lyophilized.

The lyophilized samples were stored in an incubator at 60° C. and removed from the incubator after 1, 2, 3, 4, 5, and 6 weeks, respectively. 1 ml of purified water was added to each vial removed. The amount (percentage) of the hirudin variant HV1C3 remaining in the lyophilized sample was determined in the same manner as in Experiment Example 1. The results are shown in Table 5.

TABLE 5

| Concentration of tartaric acid (mM) | Remaining peptide (%) | | | | | |
|---|---|---|---|---|---|---|
| | 1 wk | 2 wks | 3 wks | 4 wks | 5 wks | 6 wks |
| 0 | 97.0 | 94.0 | 92.0 | 91.0 | 87.8 | 86.5 |
| 5 | 98.8 | 98.6 | 97.6 | 97.5 | 97.0 | 96.9 |
| 10 | 98.5 | 98.1 | 97.2 | 96.9 | 96.4 | 96.1 |
| 30 | 97.9 | 96.8 | 96.1 | 94.7 | 94.1 | 93.5 |

It can be seen from the above results that the target effect of the present invention is sufficiently exhibited when the concentration of an organic acid added is as low as 5 mM.

Experiment Example 5

In the same manner as in Experiment Example 1, hirudin variant HV1C3, purified saccharose, and mannitol were dissolved in purified water to a concentration of 6 mg/ml (0.86 mM) of hirudin variant HV1C3 and concentrations of purified saccharose and mannitol respectively shown in Table 6. The solution was adjusted to pH 5.5 using 5 mM tartaric acid to obtain a peptide solution. The peptide solutions for which the pH was adjusted and the peptide solution before pH adjustment were filtered through a 0.22 μm membrane filter. The filtrates were filled into 6 ml vials in the amount of 1 ml for each vial and lyophilized.

All lyophilized samples were stable demonstrating effectiveness of purified white sugar and mannitol as vehicles. The lyophilized samples were stored in an incubator at 60° C. and removed from the incubator after 4 and 8 weeks, respectively. 1 of purified water was added to each vial removed. Solutions further diluted 50-fold were subjected to liquid chromatography to measure a peak area percentage of isomers other than the hirudin variant HV1C3. The results are shown in Table 6.

TABLE 6

| Purified saccharose (mg/ml) | Mannitol (mg/ml) | The amount of isomers (%) | |
|---|---|---|---|
| | | 4 weeks | 8 weeks |
| 1.6 | 10 | 7.23 | 8.58 |
| — | 10 | 6.93 | 7.99 |
| 1.6 | — | 4.90 | 5.00 |
| — | — | 5.72 | 6.13 |

From these results, it can be seen that purified saccharose and mannitol exhibit almost no effect on stability. Specifically, as shown in Table 6 the difference in the amount of increase in the isomers after 4 weeks and 8 weeks is very slight, indicating that the addition of purified saccharose or mannitol does not impair the effect of an organic acid on the improvement of stability.

Experiment Example 6

Lyophilized samples including hirudin variant HV1C3 were prepared from peptide solutions with formulations shown in Table 7.

TABLE 7

| No. | Hirudin variant (mg/vial) | Purified saccharose (mg/vial) | Mannitol (mg/ml) | Tartaric acid (mM) | pH | Volume of filling (ml/vial) |
|---|---|---|---|---|---|---|
| 1 | 6 | 8 | 0 | 10 | 6.0 | 5 |
| 2 | 6 | 8 | 50 | 10 | 6.0 | 5 |
| 3 | 6 | 30 | 50 | 0 | na | 1 |
| 4 | 6 | 0 | 0 | 0 | na | 5 | na: pH was not adjusted.

The lyophilized samples were stored in an incubator at 40° C. and removed from the incubator after three months. 1 ml of purified water was added to each vial removed. Solutions further diluted 50-fold were used to measure the amount (percentage) of the hirudin variant HV1C3 remaining in the lyophilized sample in the same manner as in Experiment Example 1. Averages of three samples are shown in Table 8. Chromatograms produced in this experiment are shown in FIG. 1.

TABLE 8

| No. | Remaining peptide (%) |
|---|---|
| 1 | 98.5 |
| 2 | 98.2 |
| 3 | 96.9 |
| 4 | 90.0 |

From these results, it can be seen that the addition of an organic acid to adjust the pH to the range from 5 to 6.5 was confirmed to increase long-lasting storage stability.

INDUSTRIAL APPLICABILITY

The present invention can efficiently prevent a peptide having a sequence -Asp-Gly- or -Asu-Gly- such as desulfatohirudin or hirudin variants from becoming succinimide compound or β-rearranged compound with the passage of time, thereby increasing the stability of such a peptide. Utilization of such a peptide as a medicine can be promoted by the present invention.

What is claimed is:

1. A method for stabilizing a peptide which comprises a sequence -Asp-Gly- or -Asn-Gly- by reducing the conversion of said peptide into a succinimide compound or a β-transition compound, the method comprising:
   adding an amount of an organic-acid to a solution of said peptide comprising said -Asp-Gly- or -Asn-Gly- sequence, wherein said amount of organic acid is sufficient to reduce conversion of said peptide to a succinimide or β-transition compound;
   adjusting the pH of the solution to a pH of between 5 and 6.5, and then lyophilizing the pH-adjusted solution.

2. The method according to claim 1, wherein the peptide is a hirudin amino acid variant, and further wherein the hirudin amino acid sequence Asp-Gly- or -Asn-Gly- is preserved.

3. The method according to claim 1, wherein the peptide is a desulfatohirudin.

4. The method according to of any of claims 1–3, wherein said organic acid is a pharmaceutically acceptable dibasic or tri-basic carboxylic acid with a hydroxyl group substituted on the α-carbon of the carboxylic acid.

5. The method according to claim 4, further comprising the step of adding saccharose to said solution.

6. The method according to claim 1, wherein the pH is adjusted using an organic acid selected from the group consisting of tartaric acid, citric acid, and acetic acid.

7. The method according to claim 6, further comprising the step of adding saccharose to said solution.

8. The method according to claim 7, further comprising the step of adding mannitol to the solution.

9. A pharmaceutical composition comprising an initially lyophilized solution produced according to the method of claim 7, wherein the peptide, organic acid, saccharose, and mannitol are in a molar ratio of 1:5–100:1–500.

10. The pharmaceutical composition according to claim 9, wherein the peptide is at a concentration of 0.1–500 mg/ml.

11. The pharmaceutical composition of claim 9, wherein the organic acid comprises a pharmaceutically acceptable dibasic or tri-basic carboxylic acid with a hydroxyl group substituted on the α-carbon of the carboxylic acid.

12. The pharmaceutical composition of claim 9, wherein the organic acid is selected from the group consisting of tartaric acid, citric acid, and acetic acid.

13. The pharmaceutical composition according to claim 12, wherein the peptide is at a concentration of 0.1–500 mg/ml.

14. A pharmaceutical composition comprising an initially lyophilized solution produced according to the method of any of claims 1–3, and wherein the molar ratio of said peptide to said organic acid is 1:5–100.

15. The pharmaceutical composition according to claim 14, wherein the peptide is at a concentration of 0.1–500 mg/ml.

16. The pharmaceutical composition according to claim 14, wherein said organic acid is a pharmaceutically acceptable dibasic or tri-basic carboxylic acid with a hydroxyl group substituted on the α-carbon of the carboxylic acid.

17. The pharmaceutical composition according to claim 14, wherein the organic acid is selected from the group consisting of organic acid selected from the group consisting of tartaric acid, citric acid, and acetic acid.

18. The pharmaceutical composition according to claim 14, wherein said lyophilized solution further comprises saccharose.

19. The pharmaceutical composition according to claim 18, wherein said lyophilized solution further comprises mannitol.

20. A pharmaceutical composition comprising an initially lyophilized solution produced according to the method of claim 19, wherein the peptide, organic acid, saccharose, and mannitol are in a molar ratio of 1:5–100:1–500 10–1000.

21. A pharmaceutical composition comprising an initially lyophilized solution produced according to claim 18, wherein the peptide, organic acid and saccharose are in a molar ratio of 1:5–100:1–500 10–1000.

22. The pharmaceutical composition according to claim 21, wherein the organic acid is a pharmaceutically acceptable dibasic or tri-basic carboxylic acid with a hydroxyl group substituted on the α-carbon of the carboxylic acid.

23. The pharmaceutical composition according to claim 21, wherein the organic acid is selected from the group consisting of tartaric acid, citric acid, and acetic acid.

24. The pharmaceutical composition according to claim 18, wherein said organic acid is a pharmaceutically acceptable dibasic or tri-basic carboxylic acid with a hydroxyl group substituted on the α-carbon of the carboxylic acid.

25. The pharmaceutical composition according to claim 24, wherein said lyophilized solution further comprises mannitol.

26. The pharmaceutical composition according to claim 18, wherein the organic acid is selected from the group consisting of tartaric acid, citric acid, and acetic acid.

27. The pharmaceutical composition according to claim 26, wherein said lyophilized solution further comprises mannitol.

* * * * *

UNITED STATES PATENT AND TRADEMARK OFFICE
CERTIFICATE OF CORRECTION

PATENT NO.    : 6,274,553 B1
DATED         : August 14, 2001
INVENTOR(S)   : Furuya et al.

It is certified that error appears in the above-identified patent and that said Letters Patent is hereby corrected as shown below:

Column 12,
Line 63, delete "1:5-100:1-500" and insert -- 1:5-100:1-500:10-1000 --.

Column 14,
Line 4, please delete "1:5-100:1-500 10-1000" and insert -- 1:5-100:1-500:10-1000 --.
Line 8, please delete "10-1000".

Signed and Sealed this

Twelfth Day of August, 2003

JAMES E. ROGAN
*Director of the United States Patent and Trademark Office*

SEQUENCE LISTING

<160> NUMBER OF SEQ ID NOS: 7

<210> SEQ ID NO 1
<211> LENGTH: 66
<212> TYPE: PRT
<213> ORGANISM: Artificial Sequence
<220> FEATURE:
<223> OTHER INFORMATION: Description of Artificial Sequence:Hirudin variant

<400> SEQUENCE: 1

Val Val Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

Gln Ser His Asn Gln Gly Asp Phe Glu Pro Ile Pro Glu Asp Ala Tyr
        50                  55                  60

Asp Glu
 65

<210> SEQ ID NO 2
<211> LENGTH: 65
<212> TYPE: PRT
<213> ORGANISM: Artificial Sequence
<220> FEATURE:
<223> OTHER INFORMATION: Description of Artificial Sequence:Hirudin variant

<400> SEQUENCE: 2

Ile Ile Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

Gln Ser His Asn Asp Gly Asp Phe Glu Glu Ile Pro Glu Glu Tyr Leu
        50                  55                  60

Gln
 65

<210> SEQ ID NO 3
<211> LENGTH: 65
<212> TYPE: PRT
<213> ORGANISM: Artificial Sequence
<220> FEATURE:
<223> OTHER INFORMATION: Description of Artificial Sequence:Hirudin
      variant

<400> SEQUENCE: 3

Val Val Tyr Thr Asp Cys Thr Glu Ser Gly Gln Asn Leu Cys Leu Cys
 1               5                  10                  15

Glu Gly Ser Asn Val Cys Gly Gln Gly Asn Glu Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
 65

<210> SEQ ID NO 4
<211> LENGTH: 65
<212> TYPE: PRT
<213> ORGANISM: Artificial Sequence
<220> FEATURE:
<223> OTHER INFORMATION: Description of Artificial Sequence:Hirudin
      variant

<400> SEQUENCE: 4

Ile Ile Tyr Thr Asp Cys Thr Glu Ser Gly Gln Asn Leu Cys Leu Cys
 1               5                  10                  15

Glu Gly Ser Asn Val Cys Gly Gln Gly Asn Glu Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
 65

<210> SEQ ID NO 5
<211> LENGTH: 66
<212> TYPE: PRT
<213> ORGANISM: Artificial Sequence
<220> FEATURE:
<223> OTHER INFORMATION: Description of Artificial Sequence:Hirudin
      variant

<400> SEQUENCE: 5

Ile Ile Tyr Thr Asp Cys Thr Glu Ser Gly Gln Asn Leu Cys Leu Cys
 1               5                  10                  15

Glu Gly Ser Asn Val Cys Gly Gln Gly Asn Glu Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Gln Gly Asp Phe Glu Pro Ile Pro Glu Asp Ala Tyr
    50                  55                  60

-continued

```
Asp Glu
 65

<210> SEQ ID NO 6
<211> LENGTH: 66
<212> TYPE: PRT
<213> ORGANISM: Artificial Sequence
<220> FEATURE:
<223> OTHER INFORMATION: Description of Artificial Sequence:Hirudin
      variant

<400> SEQUENCE: 6

Ile Ile Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Gln Gly Asp Phe Glu Pro Ile Pro Glu Asp Ala Tyr
    50                  55                  60

Asp Glu
 65

<210> SEQ ID NO 7
<211> LENGTH: 65
<212> TYPE: PRT
<213> ORGANISM: Artificial Sequence
<220> FEATURE:
<223> OTHER INFORMATION: Description of Artificial Sequence:Hirudin
      variant

<400> SEQUENCE: 7

Val Val Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Tyr Tyr Tyr Leu
    50                  55                  60

Gln
 65
```